(12) United States Patent
Greenberg et al.

(10) Patent No.: US 7,776,052 B2
(45) Date of Patent: *Aug. 17, 2010

(54) MEDICAL GRASPING DEVICE

(75) Inventors: Roy K. Greenberg, Bratenahl, OH (US); Krasnodar Ivancev, Lund (SE); Ram H. Paul, Jr., Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 108 days.

This patent is subject to a terminal disclaimer.

(21) Appl. No.: 10/003,011

(22) Filed: Nov. 1, 2001

(65) Prior Publication Data

US 2002/0107526 A1     Aug. 8, 2002

Related U.S. Application Data

(60) Provisional application No. 60/245,811, filed on Nov. 3, 2000.

(51) Int. Cl.
*A61F 11/00* (2006.01)
(52) U.S. Cl. .................................................. 606/108
(58) Field of Classification Search ............... 606/113, 606/1, 151, 127, 198, 213, 159, 106, 108, 606/114, 207, 200; 604/537, 523; 623/1.11
See application file for complete search history.

(56) References Cited

U.S. PATENT DOCUMENTS

| | | | |
|---|---|---|---|
| 1,225,771 A | 5/1917 | Clare | |
| 2,087,108 A | 7/1937 | Irvine | |
| 2,856,933 A | 1/1958 | Hildebrand et al. | |
| 3,828,790 A | 8/1974 | Curtiss et al. | |
| 3,868,956 A | 3/1975 | Alfidi et al. | |
| 4,046,149 A | 9/1977 | Komiya | |

(Continued)

FOREIGN PATENT DOCUMENTS

DE      2540818      4/1976

(Continued)

OTHER PUBLICATIONS

Recovery of Detached Intravascular Catheter or Guide Wire Fragments A Proposed Method; J. Curry; American Journal of Roentgenology; vol. 105, No. 4; Apr. 1969; pp. 894-896.

(Continued)

*Primary Examiner*—Pedro Philogene
(74) *Attorney, Agent, or Firm*—Brinks Hofer Gilson & Lione

(57) ABSTRACT

A medical grasping device (10) for vascular use, having an outer sheath (12), an elongate control member (50) extending within an outer sheath (12) to a distal tip section (54), and a proximal control assembly (22) including an actuation section (24) joined to the elongate control member (50). Adjacent to the distal tip section (54) is a grasping portion (70,70') that is extendable from the outer sheath (12) to create loops (74,74') for grasping a target object (T) for repositioning within the vascular system, or for removal from the patient, with loops being retractable into the outer sheath to hold the target object against the device (10) during movement of the device. Elongate control member (50) is preferably a cannula or tube having a lumen (58) extending completely therethrough for placement over a guide wire (28) already in the patient.

23 Claims, 7 Drawing Sheets

U.S. PATENT DOCUMENTS

| | | | |
|---|---|---|---|
| 4,256,113 A | 3/1981 | Chamness | |
| 4,315,509 A | 2/1982 | Smit | |
| 4,425,908 A | 1/1984 | Simon | |
| 4,493,319 A | 1/1985 | Polk et al. | |
| 4,503,569 A | 3/1985 | Dotter | |
| 4,512,338 A | 4/1985 | Balko et al. | |
| 4,590,938 A | 5/1986 | Segura et al. | |
| 4,636,346 A | 1/1987 | Gold et al. | |
| 4,723,549 A | 2/1988 | Wholey et al. | |
| 4,727,873 A | 3/1988 | Mobin-Uddin | |
| 4,741,335 A | 5/1988 | Okada | |
| 4,779,616 A | 10/1988 | Johnson | |
| 4,794,928 A | 1/1989 | Kletschka | |
| 4,832,055 A * | 5/1989 | Palestrant | 128/899 |
| 4,849,032 A | 7/1989 | Kawaguchi | |
| 4,898,591 A | 2/1990 | Jang et al. | |
| 4,950,258 A | 8/1990 | Kawai et al. | |
| 4,991,602 A | 2/1991 | Amplatz et al. | |
| 5,057,114 A | 10/1991 | Wittich et al. | |
| 5,064,428 A | 11/1991 | Cope et al. | |
| 5,098,440 A * | 3/1992 | Hillstead | 606/108 |
| 5,133,733 A | 7/1992 | Rasmussen et al. | |
| 5,163,942 A | 11/1992 | Rydell | |
| 5,171,233 A | 12/1992 | Amplatz et al. | |
| 5,171,314 A | 12/1992 | Dulebohn | |
| 5,290,294 A | 3/1994 | Cox et al. | |
| 5,320,627 A | 6/1994 | Sorensen et al. | |
| 5,324,306 A | 6/1994 | Makower et al. | |
| 5,330,484 A * | 7/1994 | Gunther et al. | 606/128 |
| 5,342,371 A | 8/1994 | Welter et al. | |
| 5,354,623 A | 10/1994 | Hall | |
| 5,376,094 A * | 12/1994 | Kline | 606/113 |
| 5,387,219 A | 2/1995 | Rappe | |
| 5,397,365 A | 3/1995 | Trentacosta | |
| 5,417,684 A | 5/1995 | Jackson et al. | |
| 5,464,408 A | 11/1995 | Duc | |
| 5,484,384 A | 1/1996 | Fearnot | |
| 5,484,444 A * | 1/1996 | Braunschweiler et al. | 623/1.11 |
| 5,486,182 A | 1/1996 | Nakao et al. | |
| 5,486,183 A * | 1/1996 | Middleman et al. | 606/127 |
| 5,496,330 A | 3/1996 | Bates et al. | |
| 5,522,819 A | 6/1996 | Graves et al. | |
| 5,562,678 A | 10/1996 | Booker | |
| 5,597,378 A | 1/1997 | Jervis | |
| 5,597,387 A | 1/1997 | Bauer et al. | |
| 5,613,973 A | 3/1997 | Jackson et al. | |
| 5,626,605 A | 5/1997 | Irie et al. | |
| 5,653,716 A * | 8/1997 | Malo et al. | 606/139 |
| 5,681,347 A * | 10/1997 | Cathcart et al. | 606/200 |
| 5,713,907 A | 2/1998 | Hogendijik et al. | |
| 5,713,948 A | 2/1998 | Uflacker | |
| 5,769,830 A | 6/1998 | Parker | |
| 5,779,680 A | 7/1998 | Yoon | |
| 5,782,839 A | 7/1998 | Hart et al. | |
| 5,788,710 A | 8/1998 | Bates et al. | |
| 5,868,754 A | 2/1999 | Levine et al. | |
| 5,873,876 A | 2/1999 | Christy | |
| 5,906,622 A | 5/1999 | Lippitt et al. | |
| 5,910,144 A * | 6/1999 | Hayashi | 606/108 |
| 5,924,175 A | 7/1999 | Lippitt et al. | |
| 5,944,728 A | 8/1999 | Bates | |
| 5,947,978 A | 9/1999 | Holsinger | |
| 5,974,978 A | 11/1999 | Brown | |
| 5,989,266 A | 11/1999 | Foster | |
| 5,993,474 A * | 11/1999 | Ouchi | 606/206 |
| 6,015,415 A | 1/2000 | Avellanet | |
| 6,027,520 A | 2/2000 | Tsugita et al. | |
| 6,036,717 A | 3/2000 | Mers Kelly et al. | |
| 6,096,053 A * | 8/2000 | Bates | 606/159 |
| 6,099,534 A | 8/2000 | Bates et al. | |
| 6,156,055 A | 12/2000 | Ravenscroft | |
| 6,162,209 A | 12/2000 | Gobron et al. | |
| 6,171,327 B1 * | 1/2001 | Daniel et al. | 606/200 |
| 6,179,861 B1 | 1/2001 | Khosravi et al. | |
| 6,183,482 B1 | 2/2001 | Bates et al. | |
| 6,187,016 B1 | 2/2001 | Hedges et al. | |
| 6,187,017 B1 | 2/2001 | Gregory, Jr. | |
| 6,221,048 B1 | 4/2001 | Phelps | |
| 6,241,738 B1 | 6/2001 | Dereume | |
| 6,245,087 B1 | 6/2001 | Addis | |
| 6,264,664 B1 * | 7/2001 | Avellanet | 606/128 |
| 6,280,451 B1 | 8/2001 | Bates et al. | |
| 6,280,464 B1 | 8/2001 | Hayashi | |
| 6,325,807 B1 | 12/2001 | Que | |
| 6,336,934 B1 | 1/2002 | Gilson et al. | |
| 6,342,062 B1 | 1/2002 | Suon et al. | |
| 6,348,056 B1 | 2/2002 | Bates et al. | |
| 6,352,539 B1 | 3/2002 | Avellanet | |
| 6,364,887 B1 | 4/2002 | Dworschak et al. | |
| 6,364,895 B1 | 4/2002 | Greenhalgh | |
| 6,416,519 B1 | 7/2002 | VanDusseldorp | |
| 6,443,971 B1 * | 9/2002 | Boylan et al. | 606/200 |
| 6,447,530 B1 | 9/2002 | Ostrovsky et al. | |
| 6,458,139 B1 | 10/2002 | Palmer et al. | |
| 6,458,145 B1 | 10/2002 | Ravenscrof et al. | |
| 6,491,698 B1 | 12/2002 | Bates et al. | |
| 6,494,895 B2 | 12/2002 | Addis | |
| 6,500,182 B2 * | 12/2002 | Foster | 606/127 |
| 6,517,550 B1 | 2/2003 | Konya et al. | |
| 6,520,968 B2 * | 2/2003 | Bates et al. | 606/113 |
| 6,520,978 B1 | 2/2003 | Blackledge et al. | |
| 6,554,842 B2 | 4/2003 | Heuser et al. | |
| 6,558,404 B2 | 5/2003 | Tsukernik | |
| 6,569,181 B1 | 5/2003 | Burns | |
| 6,589,231 B1 | 7/2003 | Gobron et al. | |
| 6,599,296 B1 | 7/2003 | Gillick et al. | |
| 6,695,813 B1 * | 2/2004 | Boyle et al. | 604/106 |
| 6,695,913 B1 | 2/2004 | Duggan | |
| 6,755,847 B2 * | 6/2004 | Eskuri | 606/200 |
| 6,837,901 B2 | 1/2005 | Rabkin et al. | |
| 6,893,451 B2 | 5/2005 | Cano et al. | |
| 6,939,370 B2 | 9/2005 | Hartley et al. | |
| 7,101,379 B2 | 9/2006 | Gregory, Jr. et al. | |
| 7,322,989 B2 | 1/2008 | Teague et al. | |
| 2001/0021842 A1 | 9/2001 | Ouchi | |
| 2001/0031970 A1 | 10/2001 | Heuser et al. | |
| 2001/0044629 A1 | 11/2001 | Stinson | |
| 2002/0022837 A1 | 2/2002 | Mazzocchi et al. | |
| 2002/0026202 A1 | 2/2002 | Honey et al. | |
| 2002/0026203 A1 | 2/2002 | Bates et al. | |
| 2002/0045863 A1 | 4/2002 | Wechler | |
| 2002/0068954 A1 | 6/2002 | Foster | |
| 2002/0087186 A1 | 7/2002 | Shelso | |
| 2002/0095174 A1 | 7/2002 | Tsugita et al. | |
| 2002/0107526 A1 | 8/2002 | Greenberg et al. | |
| 2002/0120277 A1 | 8/2002 | Hauschild et al. | |
| 2002/0133168 A1 | 9/2002 | Smedley et al. | |
| 2002/0133170 A1 | 9/2002 | Tsuruta | |
| 2002/0193824 A1 | 12/2002 | Boylan et al. | |
| 2003/0109874 A1 | 6/2003 | Dennis | |
| 2003/0109889 A1 | 6/2003 | Mercereau et al. | |
| 2003/0125793 A1 | 7/2003 | Vessely | |
| 2003/0135222 A1 | 7/2003 | Baska | |
| 2003/0158518 A1 | 8/2003 | Schonholz et al. | |
| 2003/0171739 A1 | 9/2003 | Murphy et al. | |
| 2003/0195492 A1 | 10/2003 | Gobron et al. | |
| 2003/0225419 A1 | 12/2003 | Lippitt et al. | |
| 2003/0233099 A1 | 12/2003 | Danaek et al. | |
| 2004/0158275 A1 | 8/2004 | Crank et al. | |
| 2004/0230287 A1 | 11/2004 | Hartley et al. | |
| 2005/0004595 A1 | 1/2005 | Boyle et al. | |
| 2005/0038495 A1 | 2/2005 | Greenan | |
| 2005/0085846 A1 | 4/2005 | Carrison et al. | |
| 2006/0030865 A1 | 2/2006 | Balg | |

| | | | |
|---|---|---|---|
| 2006/0052797 | A1 | 3/2006 | Kanamaru |
| 2006/0064113 | A1 | 3/2006 | Nakao |
| 2006/0106417 | A1 | 5/2006 | Tessmer et al. |

FOREIGN PATENT DOCUMENTS

| | | | | |
|---|---|---|---|---|
| DE | 3029064 | | 2/1982 | |
| DE | 3804849 | | 9/1988 | |
| DE | 4115136 | * | 11/1991 | ................ 606/108 |
| DE | 4115136 | | 11/1992 | |
| EP | 0472368 | * | 2/1992 | ................ 606/108 |
| FR | 724776 | | 1/1932 | |
| WO | 9916363 | | 4/1999 | |
| WO | 9948429 | | 9/1999 | |
| WO | 0033909 | | 6/2000 | |

OTHER PUBLICATIONS

Retrieval of a Ventriculoatrial Shunt Catheter from the Heart by a Venous Catheterization Technique; T. Tatsumi & W. Howland; Journal of Neurosurgery; vol. 32; May 1970; pp. 593-595.

The Nonsurgical Retrieval of Intracardiac Foreign Bodies—An International Survey; D. Bloomfield; Catherterization and Cardiovascular Diagnosis; vol. 4; 1978; pp. 1-14.

"*Günther Tulip Vena Cava Filter Set Jugular Vein Approach*;" William Cook Europe, 2003 Product Catalog.

"*New Retrievable Percutaneous Vena Cava Filter*: Experimental In Vitro and In Vivo Evaluation;" Jörg Neuerburh, Rolf Günther, Erik Rassmussen, Dierk Vorwerk, Kirsten Tonn, Stefan Handt, Werner Küpper, J. Vagn Hansen, vol. 16, No. 4, Jul./Aug. 1993.

"*An Improved Snare System for the Nonsurgical Retieval of Intravascular Foreign Bodies;*" John W. Hubert, MD; Ronald J. Krone, MD, FSCA; Burton A. Shatz, MD; and Noah Susman, MD, Catheterization and Cardiovascular Diagnosis, 6:405-411 (1980).

Office Action Dated Feb. 22, 2008, Corresponding to U.S. Appl. No. 10/828,094.

Office Action Dated Jan. 11, 2008, Corresponding to U.S. Appl. No. 10/814,018.

Office Action Dated Jun. 3, 2008, Corresponding to U.S. Appl. No. 10/814,089.

Office Action Dated Oct. 30, 2007, Corresponding to U.S. Appl. No. 10/814,989.

United States Patent and Trademark Office Action for U.S. Appl. No. 10/828,094 Dated Feb. 3, 2009.

United States Patent and Trademark Office Action for U.S. Appl. No. 10/814,018 Dated Feb. 25, 2009.

Notice of Allowance for U.S. Appl. No. 10/814,018 dated Sep. 21, 2009.

Notice of Allowance for U.S. Appl. No. 10/828,094 dated Aug. 25, 2009.

Written Opinion Issued on PCT/US07/006890, Dated Sep. 20, 2008.

International Search Report on PCT/US07/006890, Dated Sep. 24, 2007.

* cited by examiner

MEDICAL GRASPING DEVICE

RELATED APPLICATION INFORMATION

This application claims priority to U.S. Provisional Patent Application Ser. No. 60/245,811 filed Nov. 3, 2000.

TECHNICAL FIELD

This invention is related to medical devices and in particular to a medical grasping device.

BACKGROUND OF THE INVENTION

There is a current trend in medicine to minimize surgical and interventional procedures, concomitant with the development of minimally invasive tools to access, visualize, infuse, treat, medicate, sample, and interact with internal structures of the body. Occasionally, devices such as catheters, balloons or wires are inadvertently severed in a blood vessel, cavity or organ. Depending on its location, the severed device or fragment must be retrieved. Frequently, a surgical approach is dangerous and costly. In many cases, access has already been established to the severed device, fragment, or foreign body in question, and it is just a matter of locating and removing the foreign body without doing harm to surrounding tissue or forcing it further out of reach.

Certain medical devices are known that are utilized in the ducts and vessels of a human or veterinary patient for retrieval of bodies from the patient. For example, retrieval devices are known for removing calculi such as kidney stones or gallstones from a patient, where the retrieval device is delivered to the target site via the urethra or biliary duct, respectively. The device's distal tip is adapted to deploy at the site to form a basket shape to trap the calculi after which the basket is collapsed to grasp the calculi. Both the device and the grasped calculi are then withdrawn from the patient.

One such stone retrieval device is disclosed in U.S. Pat. No. 5,989,266, in which several loops of wire are caused to emerge from the distal end of a sheath that has previously been delivered through the renal or biliary system of a patient to the site of the stone. The stone becomes trapped within the loops, after which the loops are pulled proximally mostly into the sheath, grasping the stone firmly, after which the sheath, loops and stone are withdrawn from the patient. The loops are disclosed to be made from a superelastic alloy such as nitinol to automatically form the loops when caused to emerge from the sheath's distal tip. Other similar stone retrieval devices are disclosed in U.S. Pat. Nos. 5,057,114; 5,064,428; 5,133,733 and 5,484,384.

However, use of such devices is not satisfactory for grasping such an object within the vascular system of a patient for repositioning of that object, or for removal of objects from within the vascular system of a patient. For example, in certain situations it is desired to reposition a stent or stent graft within the vasculature, or to retrieve or reposition a malpositioned or misplaced embolization coil. And during delivery and deployment of a bifurcated stent graft at the site of an abdominal aortic aneurysm when surgical access has been obtained through the femoral arteries on both sides of the groin, it is desirable to grasp the distal tip of a guide wire extending into the aneurysm from the contralateral iliac artery, to be pulled into the ipsilateral iliac artery at the vessel's aorto-iliac bifurcation, for eventual placement of the contralateral leg extension of the stent graft.

For vascular use, another known device is a suture loop a catheter distal tip. Yet another is a guide wire that has been doubled over and extended through a catheter so that its distal end forms into a loop that extends axially from the catheter's distal end to be utilized as a retriever when it is pulled proximally to capture an object and hold it against the catheter distal end for withdrawal, sold as the Curry Intravascular Retriever Set by Cook, Incorporated, Bloomington, Ind. A version of the stone basket device, having helical loops, has been utilized for intravascular retrieval, the Dotter Intravascular Retriever Set also sold by Cook, Incorporated.

In U.S. Pat. No. 5,171,233 is disclosed a snare-type probe for intravascular use. After a catheter is inserted into the patient's vascular system to the site of the foreign object, an elongate member having a loop-shaped distal segment is inserted into the proximal end of the catheter's lumen until the loop-shaped distal segment emerges from the catheter's distal tip at the site. Then the loop-shaped segment extends at an angle to the adjacent portion of the member and opens into a loop. Once a free end of the foreign object is snared within the loop-shaped distal segment as determined by fluoroscopic equipment, the loop-shaped distal segment is pulled proximally into the catheter distal end, collapsing about the ensnared foreign body fragment and holding the foreign body at the distal tip of the catheter during withdrawal. The elongate member is preferably disposed within an outer sheath and is disclosed to be one wire, or two gripped-together wires, of a shape memory material such as a superelastic nitinol alloy, with a single preformed loop shape at the distal segment defined by two wire portions. The use of nitinol enables the wire segments defining the distal segment to be straightened and collapsed upon one another into an elastically deformed configuration to pass through the lumen of the catheter and yet automatically open into a loop and extend at a substantial angle upon emerging from the catheter distal tip. One characteristic of this design is that during retraction after grasping, the loop quickly changes, or "flips," between the angled orientation and a generally axial one, and this results in less assured control over the item during grasping, and commonly will result in escape of the item thus requiring redeployment of the loop for another grasping attempt.

It is desired to provide a medical grasping device for grasping and repositioning an object within the vascular system of a patient, such as a stent or stent graft or embolization coil or such as the distal tip of a catheter or a guide wire; or to grasp a stent or embolization coil, or a fragment from a catheter or guide wire or a pacemaker lead, for its removal from the patient.

It is also desired to provide a low profile, medical grasping device that is conformable to the vascular anatomy while generating a substantial tensile force.

It is further desired to provide such a device that is trackable through the vascular system over a guide wire already in situ.

It is yet further desired to provide such a device that is atraumatic to the patient.

SUMMARY OF THE INVENTION

The foregoing problems are solved and a technical advance is achieved in an illustrative embodiment of a medical grasping device of the present invention. The grasping device includes an outer sheath and an elongate control member that is relatively axially movable with respect thereto within a passageway of the outer sheath when actuated by a proximal control assembly. In a first aspect of the present invention, when in the retracted state, an atraumatic distal tip section of the elongate control member extends forwardly beyond the distal end of the outer sheath, especially of value during placement of the grasping device within the vascular system of a patient to reach the target site of the object to be grasped. Just proximal of the atraumatic distal tip section is the grasping portion of the device, restrained within the distal end portion of the outer sheath until actuated.

In a second aspect, preferably, the grasping portion defines a plurality of preformed wire loops that smoothly deploy laterally when the elongate control member is moved distally urging the wires to emerge from the distal end of the outer sheath, and that smoothly resume an axial orientation when being retracted into the outer sheath while the loops are being reduced in size, thus assuredly snaring the object.

In a third aspect of the invention, the wire loops are formed from a superelastic alloy such as nitinol, so that the loops are easily collapsible for insertion into the outer sheath and movement therealong during assembly, and for actuation and later retraction into the outer sheath distal end after grasping, and so that the loops automatically form upon actuation of the device and emerging from the outer sheath distal end to traverse the cross-section of the vessel. The wire segments are affixed to the distal portion of the elongate control member, where the elongate control member is preferably of a different material.

In a fourth aspect of the invention, the grasping portion comprises a plurality of loops, such as preferably four loops that define a clover-leaf shape, that extend at a substantial angle to the axis of the cannula, and preferably transverse thereto upon full deployment so that the four loops together generally occupy the full cross-section of the vessel. As the loops are emerging from the sheath distal end, the wire segments initially are axially oriented but begin to deflect radially and diverge from one another as the loops begin to open. Preferably, even when the loops are fully formed and transversely oriented, the segments of the wires forming the loops extend in a continuous fashion to axially aligned end portions at the affixation joints with the elongate control member. Where the vessel diameter is less than the general outer envelope formed by the four loops if deployed when fully unrestrained, the loops will generally fill the vessel until engagement with the vessel walls inhibits full transverse orientation whereupon the loops are angled and opened.

In a fifth aspect of the invention, the elongate control member is preferably a flexible cannula or tube defining a lumen extending therethrough for a guide wire to be received thereinto, for placement onto and passage of the device over a guide wire so that the grasping device is easily and quickly guided to the treatment site by a guide wire already in place in the patient. The lumen extends through the grasping portion and the atraumatic distal tip section so that the device is insertable over the exposed proximal end of the guide wire that is already in situ. Such an over-the-wire advantage: allows access to tortuous anatomy and multiple side branches; obviates the need to remove the guide wire to permit insertion of the grasping device into the patient; obviates the otherwise tedious procedure of guiding (without the benefit of guidance and support of a guide wire) the outer sheath device through the vasculature of the patient to the target site; and obviates the need to later reinsert the previously-removed guide wire following eventual removal of the grasping device, for possible additional treatment procedures of various kinds; and all thereby results in much-reduced treatment time and much-reduced risk to the patient.

In a sixth aspect of the invention, the grasping device preferably includes hemostatic sealing between the outer sheath and the elongate control member.

In additional aspects, the grasping device includes a proximal control assembly that is easily manipulated for actuation during grasping, and for assured continued automatic grasping of the object with a controlled, limited amount of force while the device is being moved to manually reposition the object or to remove it completely. The elongate control member is formed to have torqueability and significant tensile strength with low elongation. The outer sheath has a flexible but kink-resistant construction with lubricious outer and inner surfaces.

BRIEF DESCRIPTION OF THE DRAWING

Embodiments of the present invention will now be disclosed by way of example with reference to the accompanying drawings, in which.

DETAILED DESCRIPTION

Figure 1:
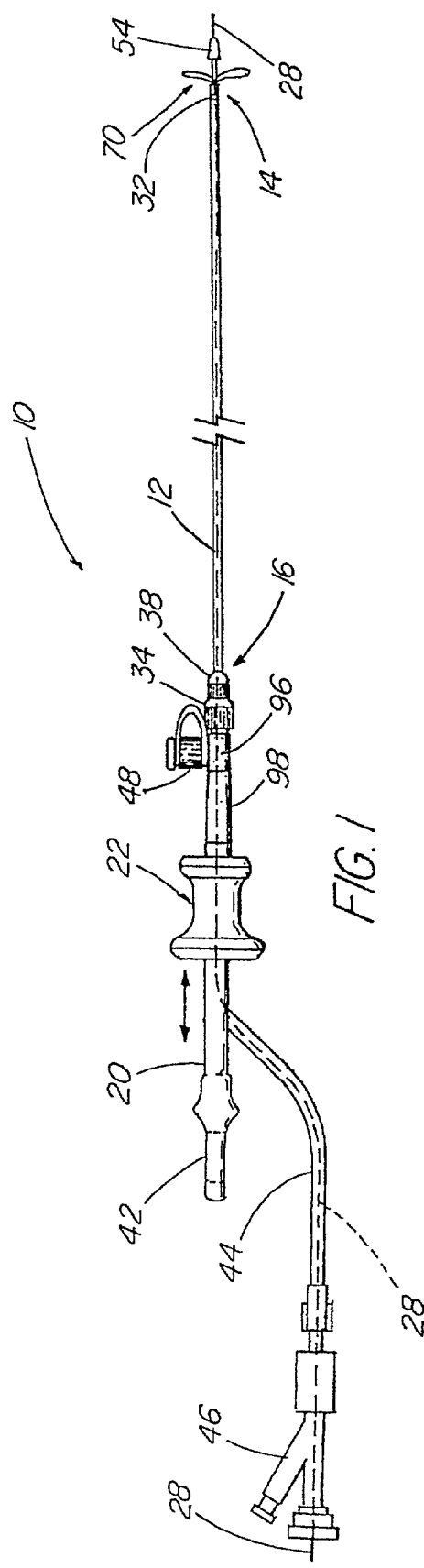
FIG. 1 is an elevation view of the grasping device of the present invention.
Figure 2:
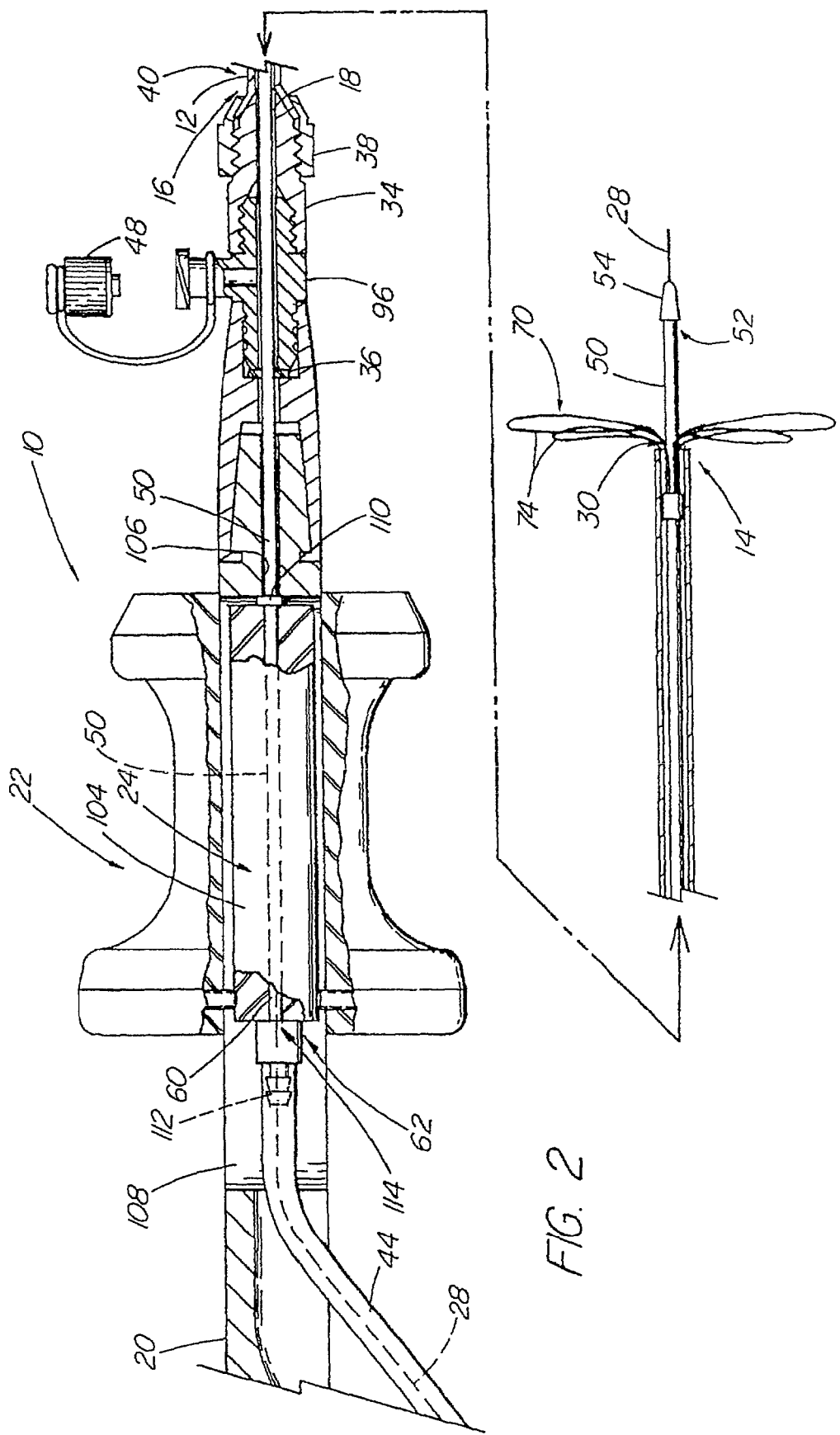
FIG. 2 is an enlarged partial section view of the device of FIG. 1.
Figure 3:
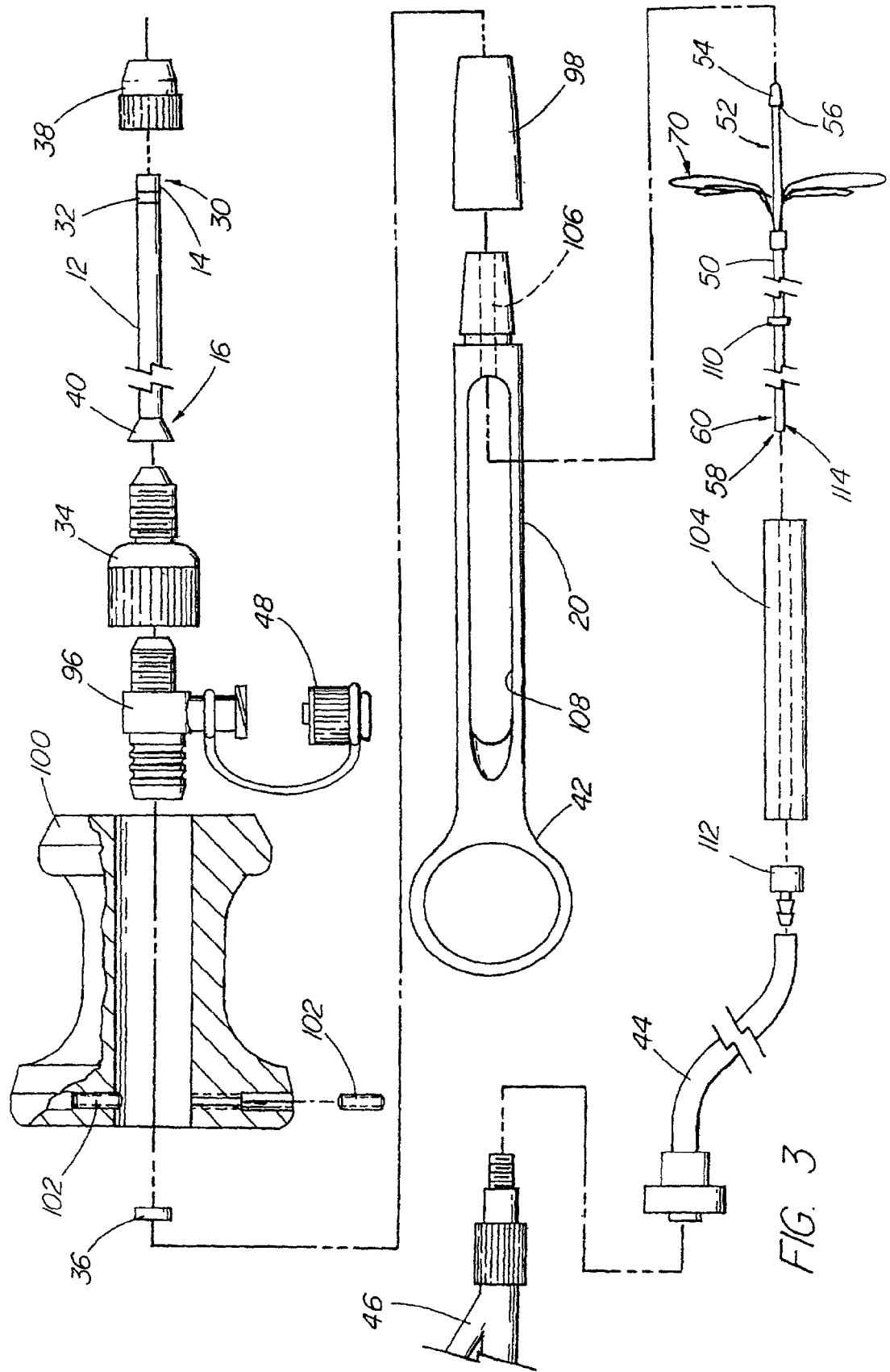
FIG. 3 is an exploded elevation view showing the components of the grasping device of FIGS. 1 and 2.

With regard to FIGS. 1 to 3, grasping device 10 of the present invention includes an outer sheath 12 extending from a distal end portion 14 to a proximal end 16. Secured to the proximal end 16 is proximal control assembly 22 including a handle 20 that is affixed to the outer sheath 12. Proximal control assembly 22 also includes an actuation section 24 that is movably affixed to the handle 20, and that is in operative relationship with an elongate control member 50 that is disposed within outer sheath 12 and extends along passageway 18 completely therethrough to a distal end portion 52 that is adjacent to distal end portion 14 of outer sheath 12. Outer sheath 12 also includes adjacent to its distal end 30 a radiopaque marker band 32. Distal end portion 52 of control member 50 concludes in a distal tip section 54, and spaced proximally from the proximal end 56 of distal tip section 54 is the grasping portion 70 of the present invention.

Elongate control member 50 is preferably a cannula or tube having a guide wire lumen 58 extending completely therethrough, for receipt therethrough of a guide wire 28. Guide wire 28 need not be part of the grasping device 10 of the present invention, but the present invention is particularly designed to be used therewith and would be of the type conventionally in use for various intravascular procedures. Elongate control member 50 has an outer diameter that is less than the inner diameter of passageway 18 to enable relative axial movement within the outer sheath 12 when actuated. Elongate control member 50 has a distal tip section 54 that is blunt and rounded to be atraumatic to the patient, preferably tapered to its rounded tip from the outer surface of outer sheath 12 at distal sheath end 30 to provide a smooth transition between the outer sheath and the guide wire 28. The atraumatic tip protects the vessel wall and reduces the chance that the distal tip of the grasper device will shear off any atheromatous plaque that it encounters while tracking through the vascular vessel. At proximal end portion 60 of elongate control member 50 is a connection 62 to actuation section 24.

A side flushport fitting 96 with a T-shaped lumen therein is affixed to the front end of handle 20 such as by snap coupling 98 and secures therewithin a seal 36 surrounding control member 50, such as a flat flexible sealing washer, and holds it tightly against the front end of handle 20. Seal 36 defines hemostatic sealing of passageway 18 around control member 50. A cap 38 attaches outer sheath 12 to a threaded forward portion of adapter fitting 34. Cap 48 keeps the lumen of flushport fitting 96 sealed when not connected to a fluid source. Preferably, outer sheath 12 includes an enlarged or flared proximal end 40 on proximal end 16 that is tightly gripped by cap 38, and enlarged proximal end 40 may be complementary to a conical forward end of threaded forward portion of fitting 34. Handle 20 preferably includes a thumb ring 42. Seen extending rearwardly and at a gradual angle laterally from handle 20 is tubing 44 that is affixed to the rearward end of control member 50 and having a passageway along which guide wire 28 extends, with tubing 44 including thereon a Touhy-Borst adaptor 46, for hemostatic sealing around the guide wire proximally of control member 50.

Figure 4:
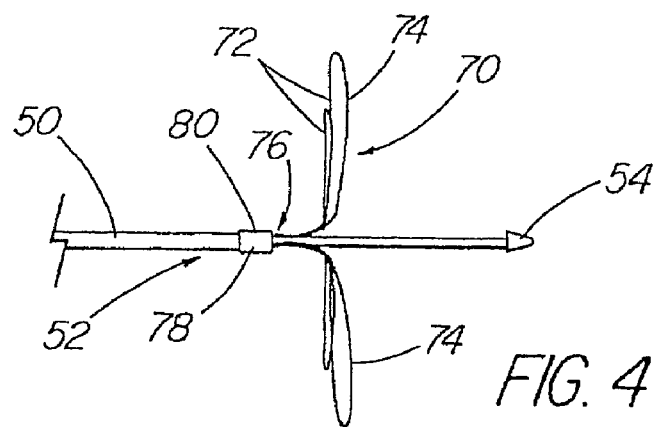
FIG. 4 is an enlarged view of the grasping portion of the device.
Figure 5:
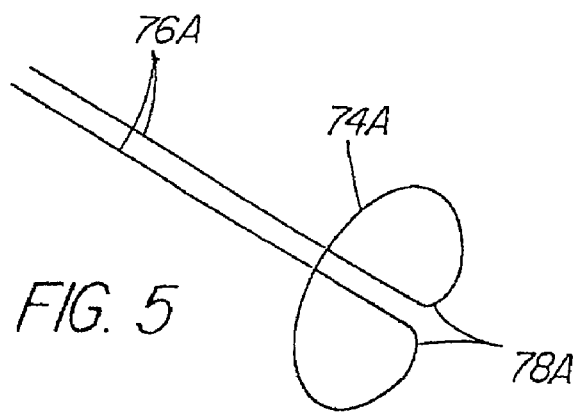
FIG. 5 is an isometric view illustrating one of the wire segments defining one of the loops.

Referring now to FIGS. 4 and 5, the grasping portion 70 is preferably defined by wire segments 72 that define loops 74. Wire segments 72 are preferably fabricated from a superelastic material such as nitinol. Proximal ends 76 of the wire segments may be affixed to the control member at affixation joints 78, such as by low-temperature soldering as in U.S. Pat. No. 5,354,623, or, less preferably, welding to a stainless steel band 80 that is affixed to distal end portion 52 of control member 50 such as by crimping or bonding.

Figure 8:
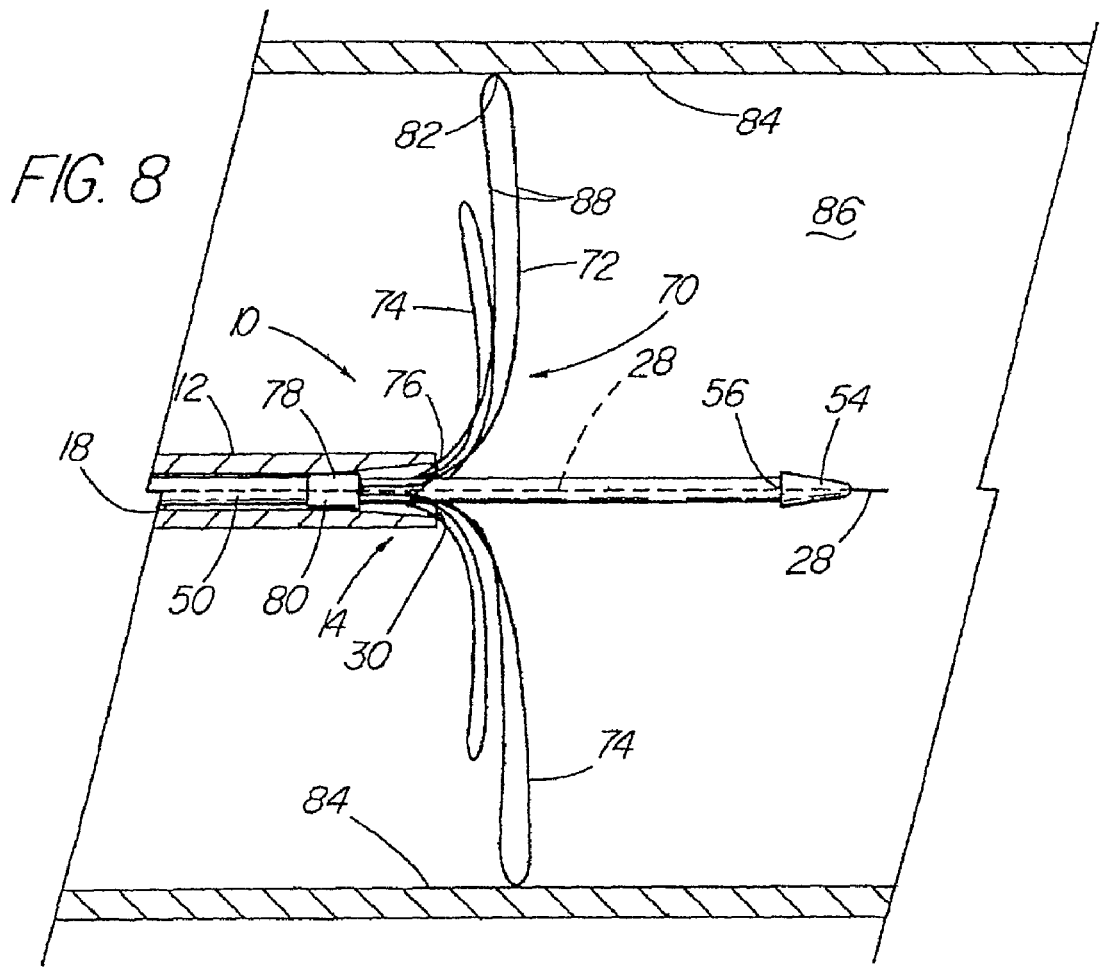

As depicted in FIG. 8, each loop 74 of grasping portion 70 includes arcuate outer sections 82 that extend to be adjacent or in abutment with wall 84 of vessel 86. Each loop 74 also includes arcuate side sections 88 that extend toward the axial center of the grasping portion 70 and then curve gradually toward the distal end of the control member and affixation joints 78. Preferably, wire segment proximal ends 76 coextend coaxially at least distally along the outer surface of the control member 50 from the affixation joints 78, and continuously and gradually extend to those portions that will define loops 74 upon emerging from outer sheath 12 upon actuation. Also, preferably, proximal ends 76 that are affixed to the control member are within the cold-worked bend 74A of the nitinol wire segment (FIG. 5), since this assures the gradual curving of that portion of loop 74 adjacent the axis as it emerges from the distal end of the outer sheath. As depicted in FIG. 5, fabrication of the affixation joints may be most easily accomplished if the wire segment 72 initially includes unbent straight segments 76A extending from ends 78A of loop 74A for ease in controlled forming, handling and positioning of the wire segment, after which at least most of segments 76A are removed.

Soldering of nitinol to stainless steel is disclosed in U.S. Pat. No. 5,354,623. Wire segment proximal ends 76 may also be secured by bonding or another form of affixation directly to control member 50 or to another intermediate member similar to band 80. Forming of the wire loops from nitinol may be attained by stress-inducing the wires into that shape during heat treatment or annealing of the grasping portion in the loop shape to create stress-induced martensite (SIM) at the loops as disclosed in U.S. Pat. No. 5,597,378 while the remainder of the wires has an austenitic state. The preforming of the loops may also be attained by cold-working the loops as is disclosed in PCT Publication WO 00/33909, by over-bending a wire in the austenitic state about a fixture. Cold-working permanently locks a portion of the crystalline structure of the bending zone into at least a partial martensitic condition while the unstressed portions of the wire remain in the austenitic state.

Figure 6:
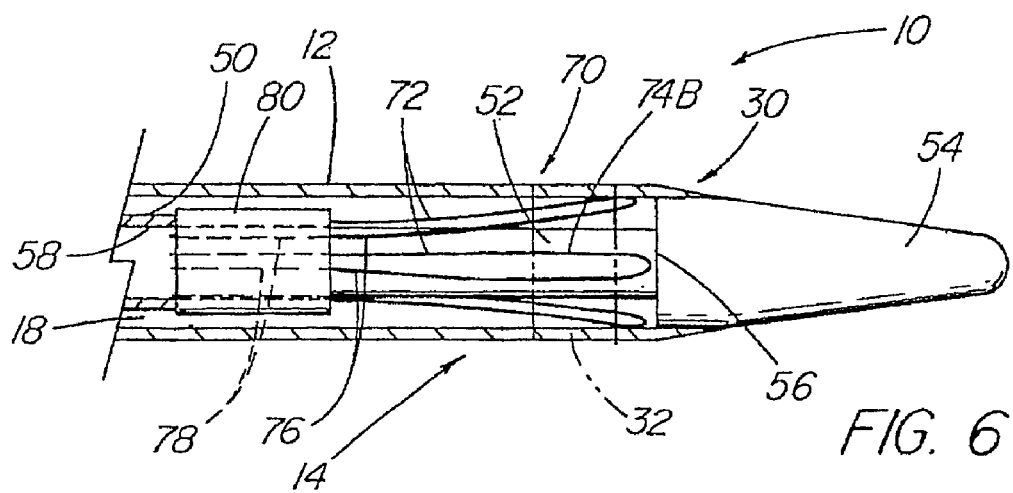
FIGS. 6 to 9 are enlarged cross-sectional views of the grasping portion and distal tip of the device prior to deployment, during deployment, fully deployed, and partially retracted after grasping a target catheter end, respectively.

Referring now to FIGS. 6 to 9, grasping portion 70 is shown in more particularity. In FIG. 6, grasping portion 70 is seen in its recessed state within distal end portion 14 of outer sheath 12, as atraumatic tip section 54 extends beyond distal sheath end 30 from control member 50. Wire segments 72 are held entirely within outer sheath 12, along distal end portion 52 of control member 50 distally of affixation joints 78 and extending axially from proximal wire portions 76. Affixation joints 78 are disposed preferably within stainless steel band 80. Loops of the wire segments 72 are seen in a constrained condition 74B along the control member just proximally of proximal end 56 of atraumatic distal tip section 54. Outer sheath 12 preferably includes a radiopaque marker band 32 around its outer surface at distal end portion 14 a small distance from sheath end 30.

Figure 7:
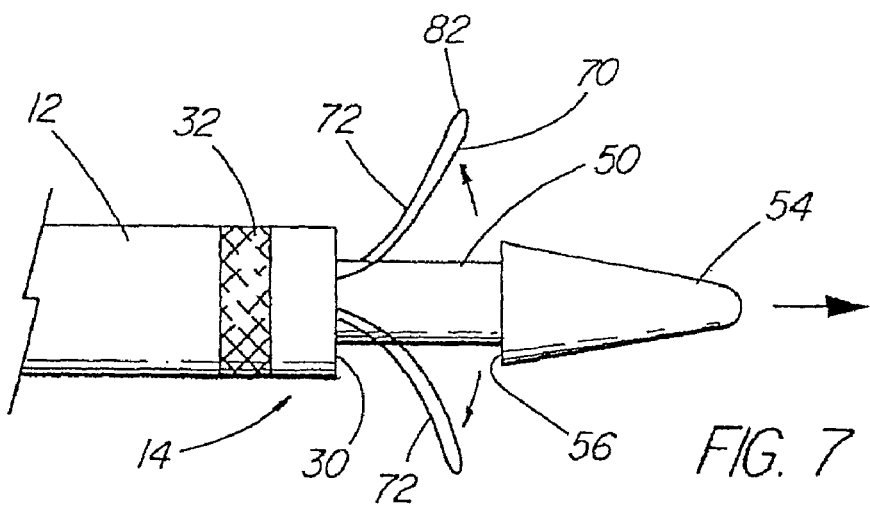

FIG. 7 illustrates partial deployment of grasping portion 70. It is clearly seen that wire segments 72 curve gradually and continuously from control member 50 forwardly and eventually radially outwardly to outer sections 82 beyond sheath end 30 during deployment as the loops 74 begin to open, and exhibit a corollary curving during retraction into outer sheath 12.

In FIG. 8 is seen grasping portion 70 fully deployed within vessel 86, with outer sections 82 of loops 74 abutting vessel wall 84. Guide wire 28 is seen extending forwardly from atraumatic distal tip section 54. Proximal wire segment sections 76 are seen to maintain a continuous, gradual curvature as they exit from distal end 30 of outer sheath 12 to form loops 74.

Figure 9:
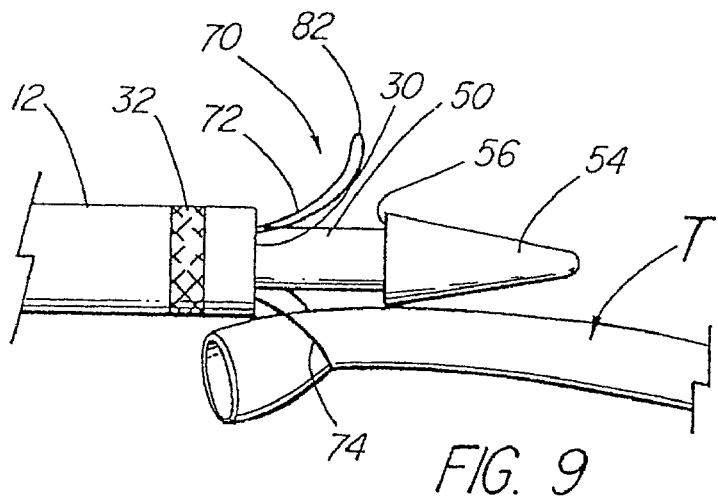

A target object T has been snared by grasping portion 70 in FIG. 9, and grasping portion 70 has been mostly retracted into outer sheath 12 so that the target object is held firmly against outer sheath 12, and nearby portions of atraumatic distal tip section 54 and possibly distal end portion 52 of control member 50 adjacent to tip section 54. In this instance, the target object is a catheter whose end portion is to be repositioned.

Figure 10:
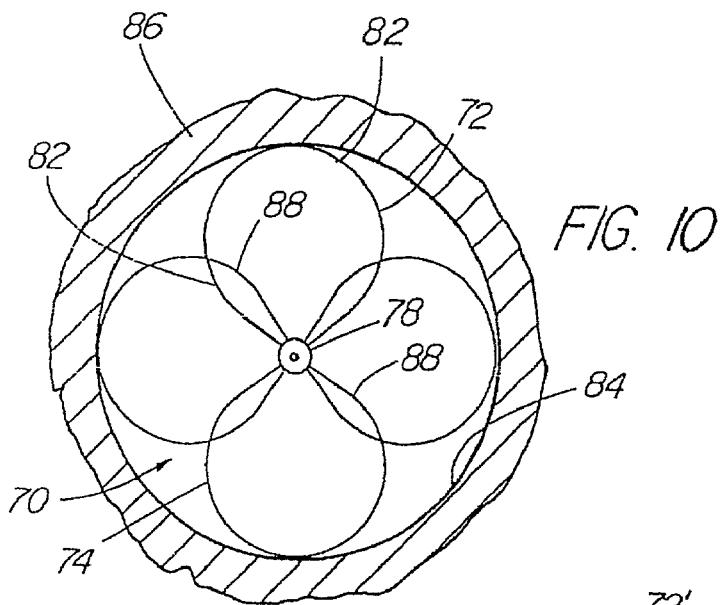
FIG. 10 is an enlarged end view of the distal end portion of the device illustrating the grasping portion of the device fully deployed.

Loops 74 are shown in FIG. 10 as substantially circular, extending to arcuate outer sections 82 with arcuate side sections 88 that extend toward the center of the grasping portion 70 and then curve toward the distal end of the control member and affixation joints 78. Side sections 88 of each loop 74 are seen to overlap to some extent with side sections 88 of adjacent loops 74. Altogether, when arcuate outer sections 82 abut the vessel wall 84 of vessel 86, the loops 74 are seen to traverse substantially the entire cross-section of the vessel.

Figure 11:
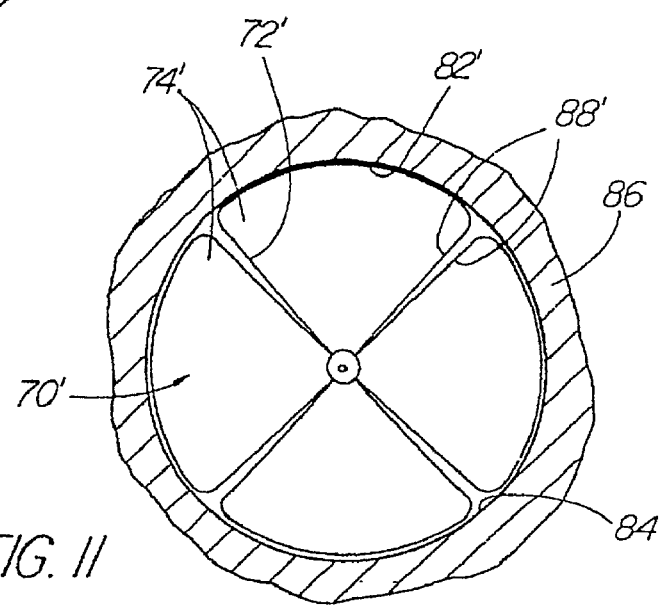
FIG. 11 is an enlarged end view of an alternate embodiment of the grasping portion of the present invention.

In FIG. 11 is shown an alternate embodiment of grasping portion 70'. Grasping portion 70' comprises four pie-shaped loops 74', each defined by wire segments 72' that preferably are superelastic material such as nitinol. Each pie-shaped loop 74' includes an outer section 82' that is arcuate for abutment against the vessel wall 84 of vessel 86 and having a radius about equal to the radius of the vessel at the target site, and opposed radial side sections 88' converging to the center of the grasping portion. It can be seen the entire cross-section of the vessel 86 is traversed by the grasping portion when deployed. As with grasping portion 70 of FIG. 10, side sections 88' may overlap those of adjacent loops 74'.

Figure 12:
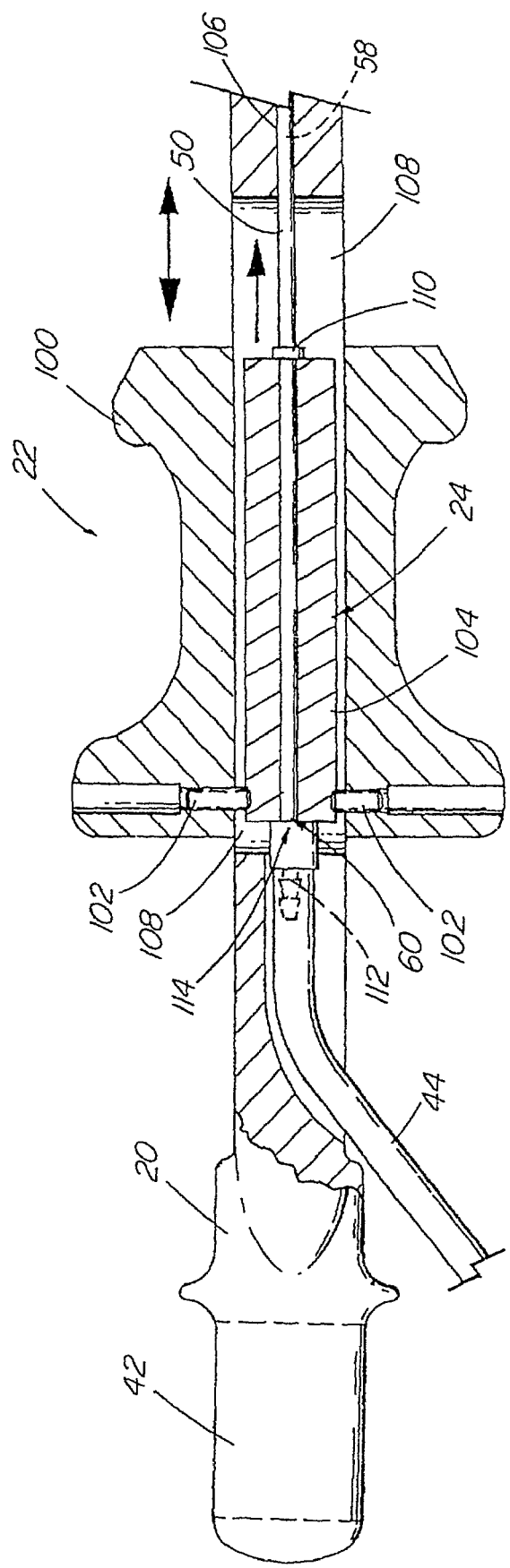
FIG. 12 is an enlarged view of the actuation section of the proximal controls.

With reference now to FIGS. 2, 3 and 12, proximal control assembly 22 is shown in greater particularity and includes an ergonomic easily grippable spool-shaped slide member 100 that is reciprocally movable along handle 20 to in turn actuate control member 50 to move with respect to outer sheath 12 attached to handle 20. Slide member 100 is fastened such as by set screws 102 to a connecting block 104 that is affixed to control member 50 extending into a central passageway 106 of handle 20 through cap 38, fitting 34 and flushport 96. Connecting block 104 is shown to be disposed within a slot 108 of handle 20. Slot 108 thus defines the limits of movement of connecting block 104 and thus of control member 50. Connecting block 104 includes an axial opening therethrough and is affixed to the proximal end of control member 50 such as by being disposed rearwardly of an annular forward stop collar 110, after which a barbed fitting 112 is placed onto the projecting rearward end 114 of control member 50 rearwardly of the connecting block 104 to form the rearward stop. Barbed fitting 112 also sealingly secures tubing 44 to rearward end 114 of control member 50. Preferably, the rearward end of slot 108 is scalloped to define a controlled shallow exit for tubing 44, through which will extend guide wire 28.

Actuation section 24 may preferably include a spring-loaded retraction section (not shown) that upon manual release thereof retracts the grasping portion 70,70' into the distal end portion 14 of the outer sheath 12, and simultaneously captures the target body T within one of the loops 74,74' so that it is held against distal sheath end 30 and distal end portion 52 of control member 50 (see FIG. 9).

The retraction section may further include a lock (not shown) that enables the grasping portion to automatically hold the grasped object T with a preselected limited grasping force during movement of the grasping device by the practitioner; such lock may be of the ratchet kind that may be manually set by the practitioner after sufficient grasping has been attained for the immediate purpose. The limited amount of force thus would protect the grasped object from damage especially were it to be of continued value in treating the patient after repositioning thereof.

Outer sheath 12 is very similar to a guiding catheter in structure and function, and may be formed for example with an inner liner of polytetrafluoroethylene and an outer jacket of a polyamide such as nylon, and may be reinforced such as by a spiral-wound flat stainless steel wire coil embedded between an inner nylon liner and an outer jacket, all in a manner disclosed in greater detail in U.S. Pat. No. 5,769,830 in order to be kink-resistant. The outer surface of the outer jacket may be coated for example with a lubricious material such as AQ™ Hydrophilic Coating. The control member 50 may be formed for example of thermoplastic material such as polyethylene terephthalate. The distal tip section 54 may be a separate member of a softer, lower durometer material of conventional composition. Lumen 58 preferably has a diameter of up to 0.040 in to allow free passage over guide wires that would have diameters of up to 0.038 in as is common.

Elongate control member 50 may be fabricated by braiding of the material in a manner that imparts the ability of the control member to be torqued, that is, to be rotated by the proximal control assembly 22 for adjusting the grasping portion about the axis, if desired. Such braiding should be from such materials and in such a manner that does not result in noticeable elongation during retraction of the grasping portion, or withdrawal of the device during total removal of the target object.

The device includes a flushport fitting to allow flushing with sterile saline solution between the elongate control member and the outer sheath to eliminate air, while the device is outside of the patient. An air seal can be utilized near the distal end of the sheath.

The grasping device of the present invention can be useful in any multiple access vascular procedure for adjusting the final position of a medical device, such as through the iliac or subclavian arteries. The invention can additionally be useful with the liver or kidney or other nonvascular procedure, especially where access to the site involves a tortuous path, since the grasping device is flexible and is adapted to follow a guide wire.

What is claimed is:

1. A medical grasping device for grasping an object comprising:
   an elongate control member continuously extending to an atraumatic distal tip section and a proximal end portion, said elongate control member further including a plurality of loops fixed to the elongate control member and located proximal said distal tip section;
   an outer sheath with a passageway therethrough surrounding said elongate control member and relatively movable with respect thereto; and
   the outer sheath and the elongate control member being relatively moveable to urge said plurality of loops from a distal end of said outer sheath and retraction thereinto, a radius of each loop expanding to overlap adjacent loops as the plurality of loops are urged distally from the distal end, the radius of each loop decreasing to tighten around the object as the plurality of loops are retracted into the outer sheath, when fully deployed each loop extending substantially perpendicular to a longitudinal axis of the elongate control member, the plurality of loops being substantially arranged in a cross-sectional region proximal from the atrumatic tip section, each loop extending radially outward from the elongate control member in the cross-sectional region and being equally spaced angularly around the elongate control member in the cross-sectional region, wherein said elongate control member is a flexible cannula defining a lumen extending therethrough into which a guide wire is receivable and movable with respect thereto.

2. The grasping device of claim 1, further comprising a hemostatic seal between said outer sheath and said elongate control member.

3. The grasping device of claim 1, wherein said outer sheath is flexible and kink-resistant and has lubricious outer and inner surfaces.

4. The grasping device of claim 1, wherein said atraumatic distal tip section tapers to a blunt and rounded tip.

5. The grasping device of claim 1, further comprising a control assembly disposed at a proximate end of said outer sheath and the elongate control member being relatively moveable to urge said plurality of loops from a distal end of said outer sheath and retraction thereinto, wherein said elongate control member is a flexible cannula defining a lumen extending therethrough into which a guide wire is receivable and movable with respect thereto;
   wherein said control assembly includes an actuation section that is easily grippable for reciprocal movement along a handle to actuate said elongate control member with respect to said outer sheath to deploy and retract said grasping portion, respectively.

6. The grasping device of claim 5, wherein said actuation section includes a connecting block affixed to said elongate control member and is disposed within a longitudinal slot of said handle and is movable along said slot between opposite ends thereof.

7. The grasping device of claim 1, wherein said plurality of loops comprises a plurality of preformed wire loops.

8. The grasping device of claim 7, wherein said plurality of wire loops self-deploy transversely upon emerging from said distal end of said outer sheath, the wire loops self-deploying transversely proximal the atraumatic distal tip section.

9. The grasping device of claim 7, wherein each of said wire loops is substantially circular upon full deployment.

10. The grasping device of claim 9, wherein each of said wire loops includes side sections wherein each side section overlaps with a side section of a different adjacent loop of the plurality of wire loops.

11. The grasping device of claim 7, wherein each of said wire loops is pie-shaped and includes arcuate outer sections having a radius that expands to a radius of a deployment site of a vessel into which the grasping device is inserted.

12. The grasping device of claim 1, wherein said plurality of loops comprises four preformed wire loops that self-deploy transversely upon emerging from said distal end of said outer sheath approximately equally spaced angularly about a longitudinal axis of said elongate control member and thereby generally expands to occupy a full cross-section of a vessel into which the grasping device is inserted.

13. The grasping device of claim 1, wherein said plurality of loops comprises a plurality of wire loops that each are formed from a superelastic alloy.

14. The grasping device of claim 1, wherein said plurality of loops having proximal end portions that are joined to said elongate control member at affixation joints and initially extend axially from said elongate control member even when said wire loops emerge from said distal end of said outer sheath and self-deploy transversely of a longitudinal axis of the grasping device.

15. The grasping device of claim 14, wherein each of said wire loops includes an arcuate outer section that upon deployment extends toward a wall of a vessel into which the grasping device is inserted.

16. The grasping device of claim 15, wherein each of said wire loops includes arcuate side sections that extend toward an axial center of said grasping portion and then curve gradually toward said distal end of said elongate control member to proximal ends that are affixed by said affixation joints thereto and are in axial alignment therewith adjacent to said affixation joints.

17. The grasping device of claim 16, wherein said wire loops comprise nitinol wire segments.

18. The grasping device of claim 17, wherein each of said wire loops including said proximal ends are within a cold-worked bend of a respective one of said nitinol wire segments.

19. The grasping device of claim 1, wherein:
said outer sheath is flexible and kink-resistant and has lubricious outer and inner surfaces;
said control assembly includes an easily grippable actuation section along a handle to actuate said elongate control member with respect to said outer sheath; and
said grasping portion comprises a plurality of preformed wire loops of nitinol that upon deployment extend generally forwardly and radially outwardly to substantially traverse the cross-sectional area of the vessel wall into which the grasping device is inserted, each of said wire loops including an arcuate outer section of complementary shape to a vessel wall portion upon deployment, and including side sections that extend toward an axial center of said grasping portion and then curve gradually toward said distal end of said elongate control member to proximal end sections that are affixed by affixation joints to said elongate control member and are in axial alignment therewith adjacent to said affixation joints.

20. The grasping device of claim 1, wherein the elongate control member being configured to transfer torque to the plurality of loops.

21. The grasping device of claim 1, wherein each of the wire loops is pie-shaped upon deployment from the distal end of the outer sheath, each wire loop having an arcuate outer section, the arcuate outer sections cooperating to form a circular perimeter substantially perpendicular to a longitudinal axis of the elongate control member, each arcuate outer section having a radius about equal to a radius of the circular perimeter, each wire loop having an opening, the openings cooperating to substantially fill the circular perimeter, further wherein moving the elongate control member distally relative to the outer sheath expands the circular perimeter and cooperatively expands the radius of the arcuate outer sections thereby increasing the openings of the wire loops to again substantially fill the circular perimeter.

22. The grasping device of claim 1, wherein the grasping portion comprises four preformed wire loops, wire segments of the four preformed wire loops being initially oriented axially to the elongate control member, the wire segments deflecting radially and diverging from one another as the four preformed wire loops begin to open, the four preformed wire loops self-deploy transversely from said distal end of said outer sheath, said four preformed wire loops after self-deploying transversely are approximately equally spaced angularly about a longitudinal axis of said elongate control member and thereby generally occupy a full cross-section of a vessel into which the grasping device is inserted.

23. A medical grasping device for grasping an object comprising:
an elongate control member having an atraumatic distal tip section and a proximal end portion, the elongate control member further including a grasping portion proximal the distal tip section;
an outer sheath with a passageway therethrough surrounding the elongate control member and relatively movable with respect thereto; and
the outer sheath and the elongate control member being relatively moveable to urge the plurality of loops from a distal end of the outer sheath and retraction thereinto; wherein:
the elongate control member is a flexible cannula defining a lumen extending therethrough into which a guide wire is receivable and movable with respect thereto;
the outer sheath is flexible and kink-resistant and has lubricious outer and inner surfaces; and
the grasping portion comprises a plurality of preformed wire loops of nitinol that upon deployment extend outwardly to traverse the cross-sectional area of the vessel wall into which the grasping device is inserted, a radius of each loop expanding to overlap adjacent loops as the plurality of preformed wire loops are urged distally from the distal end, the radius of each loop decreasing to tighten around the object as the plurality of preformed wire loops are retracted into the outer sheath, each of the wire loops including an arcuate outer section of complementary shape to a vessel wall portion upon deployment, and including side sections that extend toward an axial center of the grasping portion and curve gradually toward the distal end of the elongate control member to proximal end sections that are affixed by affixation joints to the elongate control member and are in axial alignment therewith adjacent to the affixation joints, when fully deployed each loop extending substantially perpendicular to a longitudinal axis of the elongate control member, the plurality of loops being substantially arranged in a cross-sectional region proximal from the atrumatic tip section, each loop extending radially outward from the elongate control member in the cross-sectional region and being equally spaced angularly around the elongate control member in the cross-sectional region.

* * * * *